United States Patent
Wallin et al.

(10) Patent No.: US 6,230,666 B1
(45) Date of Patent: May 15, 2001

(54) VAPORIZER

(75) Inventors: Sten Wallin, Hägersten; Ivars Alksnis, Trängsund; Håkan Hedenberg, Järfälla, all of (SE)

(73) Assignee: Siemens-Elema AB, Solna (SE)

( * ) Notice: Subject to any disclaimer, the term of this patent is extended or adjusted under 35 U.S.C. 154(b) by 0 days.

(21) Appl. No.: 09/494,685

(22) Filed: Jan. 31, 2000

Related U.S. Application Data

(63) Continuation of application No. 09/292,612, filed on Apr. 15, 1999, now abandoned.

(30) Foreign Application Priority Data

Apr. 23, 1998 (SE) .................................................. 9801429-3

(51) Int. Cl.$^7$ ...................................................... F22D 5/34
(52) U.S. Cl. ................. 122/406.3; 122/4 R; 128/204.17; 128/203.12
(58) Field of Search .................... 122/4 D, 4 R, 122/406.3; 128/204.14, 204.17, 203.12, 203.16, 203.14

(56) References Cited

U.S. PATENT DOCUMENTS

| | | | |
|---|---|---|---|
| 3,841,560 | * 10/1974 | Sielaff | 239/136 |
| 4,693,853 | * 9/1987 | Falb et al. | 128/203.14 |
| 5,062,999 | * 11/1991 | Wallroth et al. | 128/203.14 |
| 5,168,866 | * 12/1992 | Montgomery | 128/203.12 |
| 5,237,990 | * 8/1993 | Psaros et al. | 128/203.12 |
| 5,916,595 | * 7/1999 | Olsson et al. | 128/203.12 |

* cited by examiner

Primary Examiner—Gregory Wilson
(74) Attorney, Agent, or Firm—Schiff Hardin & Waite

(57) ABSTRACT

A vaporizer for vaporizing liquid anesthetic has a chamber for liquid anesthetic, a gas flow passage, a throttle in the gas flow passage, a first connection between the chamber and the gas flow passage upstream from the throttle and a second connection between the chamber and the gas flow passage downstream from the throttle. The vaporizer is more accurate and usable with different liquid anesthetics by having an outlet valve arranged by an outlet in the vaporizer, this outlet valve being regulated by the pressure upstream from the throttle.

8 Claims, 2 Drawing Sheets

VAPORIZER

The present application is a continuation of application Ser. No. 09/292,612, filed Apr. 15, 1999 (abandoned).

BACKGROUND OF THE INVENTION

1. Field of the Invention

The present invention is directed to a vaporizer for vaporizing a liquid anesthetic of the type having a chamber containing liquid anesthetic, an inlet and an outlet with a gas flow passage, containing a throttle, therebetween, and a first connection between the chamber and the gas flow passage upstream of the throttle and a second connection between the chamber and the gas flow passage downstream of the throttle.

2. Description of the Prior Art

The manual "Halothane Vaporizer 950, Enflurane Vaporizer 951, Isoflurane Vaporizer 952" describes a vaporizer of the above type. The vaporizer has a gas flow passage for a gas, a chamber for liquid anesthetic and an adjustable throttle. An opening is arranged between the gas flow passage and the chamber upstream from the adjustable throttle. Downstream from the adjustable throttle, a capillary tube is arranged with one nozzle end opening into the gas flow passage and the other end immersed in the liquid anesthetic in the chamber.

The presence of a gas flow causes pressure to drop across the adjustable throttle. The higher pressure upstream from the throttle is propagated through the opening into the chamber and exerts pressure on the surface of the liquid, forcing the liquid up into the capillary tube. The liquid is then sprayed out of the nozzle into the gas flowing in the gas flow passage and is vaporized.

The pressure drop across the throttle depends on the throttle's setting and controls the dispensing of the liquid. Changing the throttle setting makes it possible to achieve different concentrations of anesthetic in the gas.

The known ventilator has an accuracy of ±10% of the value which is set, which is an accuracy that is sufficient for all applications in conjunction with anaesthesia. This known vaporizer, however, has certain disadvantages.

One disadvantage is that each time a flow of gas is supplied to the vaporizer to dispense anesthetic, working pressure in the vaporizer needs to build up first. This causes a slight but nevertheless measurable delay in dispensing. Moreover, the chamber must fill with gas before any pressure can be exerted on the surface of the liquid. A small loss in gas volume occurs on occasions when the chamber only holds a small amount of liquid. This loss has an effect on the concentration of dispensed anesthetic.

Even if these disadvantages only have a minor, virtually insignificant, impact on vaporizer operation, additional functional refinement would still be desirable.

Another disadvantage of this known vaporizer is that it is not suitable for use with all ordinary anesthetic agents. As a result of its low boiling point, the anesthetic desflurane is particularly unsuitable for use in this known vaporizer.

SUMMARY OF THE INVENTION

An object of the present invention is to provide a vaporizer that solves the aforementioned problems.

The above object is achieved in a vaporizer of the above type which is provided in accordance with the invention, with an outlet valve that is controlled by the pressure upstream from the throttle (which is preferably adjustable). In this manner, pressure variations are avoided on the inlet side of the throttle. Instead, pressure drops on the outlet side are utilized for dispensing the liquid. When the throttle setting is changed to increase the amount dispensed, the requisite increase in the pressure drop is mainly achieved by a pressure drop downstream from the throttle and only by a minor increase in pressure upstream from the throttle.

This avoids the need to build up a working pressure before gas is dispensed. Moreover, only a small increase in the amount of gas in the chamber, distributed over a longer period of time, will be needed. By contrast, the entire chamber in the known vaporizer must fill to the working pressure every time gas is supplied.

Instead of an adjustable throttle, a fixed throttle can be used in combination with a bypass flow past the vaporizer.

Another advantage is that the vaporizer's working pressure (in absolute terms) can be raised from about 1 bar to at least 1.7 bar. This increase means that desflurane can also be used, as the higher (constant) pressure raises the boiling point of desflurane.

Allowing gas pressure upstream from the throttle to act directly on the outlet valve in order to regulate it would be particularly advantageous.

DESCRIPTION OF THE PREFERRED EMBODIMENTS

Figure 1:
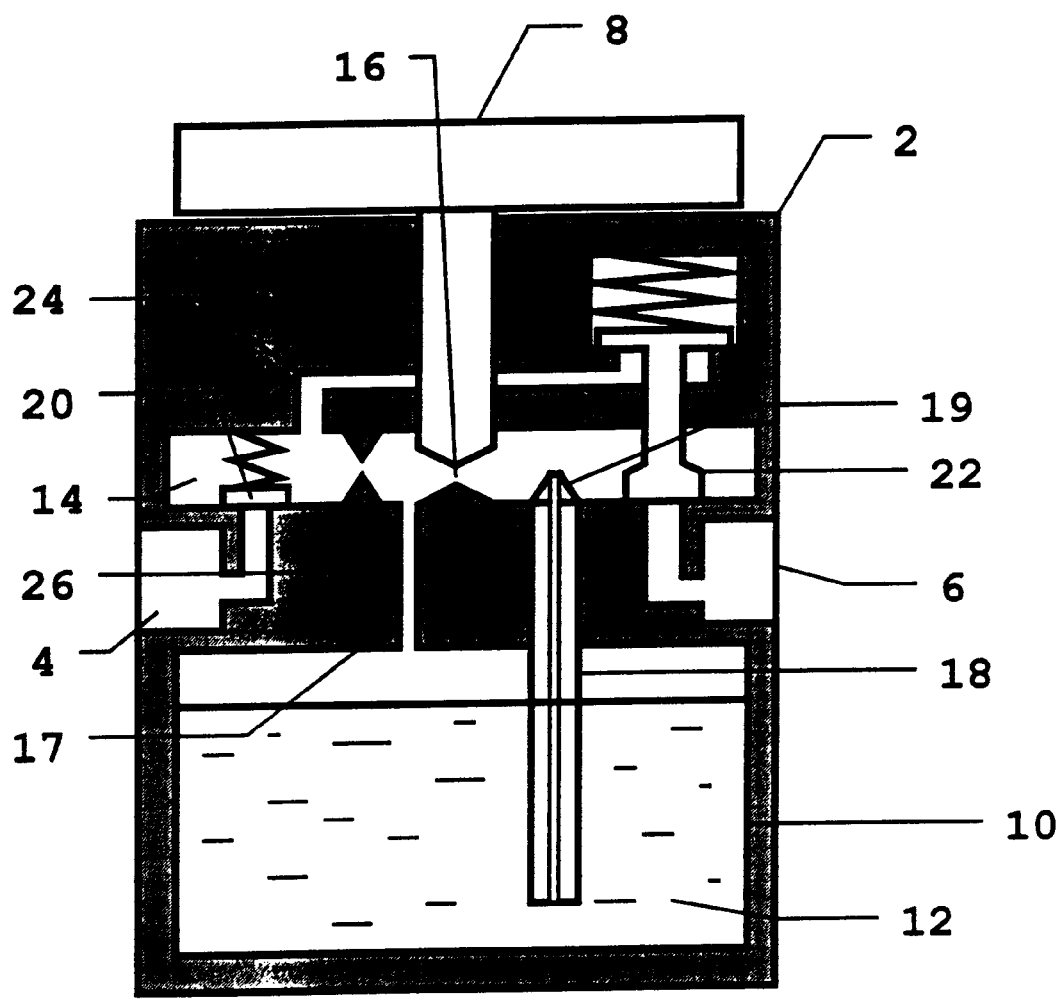
FIG. 1 shows a first embodiment of a vaporizer according to the invention.

FIG. 1 shows a first embodiment of a vaporizer 2 according to the invention. The vaporizer 2 has an inlet 4 for gas and an outlet 6 for gas and dispensed anesthetic.

The desired dose (concentration) of anesthetic is set with a control element 8.

The vaporizer 2 also has a chamber 10 for an anesthetic 12 and a gas flow passage 14. An adjustable throttle 16 is arranged in the gas flow passage 14. The control element 8 acts in this embodiment directly on the adjustable throttle 16. When a gas flow passes through the gas flow passage 14, a drop in pressure arises across the adjustable throttle 16.

A first connection 17 between the gas flow passage 14 and the chamber 10 is arranged upstream from the adjustable throttle 16. The first connection 17 opens into the gas-filled part of the chamber 10 over the surface of the anesthetic liquid 12.

A second connection between the gas flow passage 14 and the chamber 10 is arranged downstream from the adjustable throttle 16. The second connection is formed by a capillary tube 18 immersed at one end in the anesthetic 12 in the chamber. A nozzle 19 at the other end of the capillary tube 18 opens into the gas flow passage 14. The pressure drop across the adjustable throttle 16 causes gas pressure, acting on the anesthetic liquid 12 in the chamber 10, to force the anesthetic liquid through the capillary tube 18. The amount of anesthetic liquid forced into the capillary tube and out in the gas flow passage 14 through the nozzle 19 depends on the magnitude of the pressure drop.

inlet valve 20 is arranged by the inlet 4. In this instance, the inlet valve 20 is a check valve. The inlet valve 20 prevents a retrograde flow of gas through the vaporizer 2. It also facilitates maintenance of the desired pressure in the vaporizer 2.

An outlet valve 22 is arranged by the outlet 6. In this embodiment, the outlet valve 22 is a pressure regulator which, via a gas control channel 24, is connected to the space upstream from the adjustable throttle 16. The outlet valve 22 opens at a specific pressure and causes the pressure drop by means of a reduction in pressure downstream from the adjustable throttle 16.

It should be noted that gas is usually supplied to the vaporizer in pulses. The duration of these pulses of gas can vary. A normal pulse of gas can consist of about 0.3 liter of gas. When a pulse of gas, at a pressure higher than the pressure prevailing in the vaporizer 2, is delivered, the inlet valve 20 opens first to the pulse of gas. The pressure of the pulse of gas is then propagated through the gas control channel 24 to the outlet valve 22 and opens it. A pressure drop develops when the pulse of gas passes the adjustable throttle 16, and anesthetic liquid 12 is dispensed into the pulse of gas in which the liquid is vaporized and mixed. The pulse of gas and the dispensed anesthetic liquid then exit through the outlet 6, and the valves 20, 22 close at their respective closing pressures.

In this embodiment, a fixed throttle 26 is also arranged in the gas flow passage 14 between the gas control channel 24 and the first connection to the chamber 10. The fixed throttle contributes to stabilizing control of the outlet valve 22, since it causes a small primary drop in pressure before the dispensing drop in pressure across the adjustable throttle 16.

Figure 2:
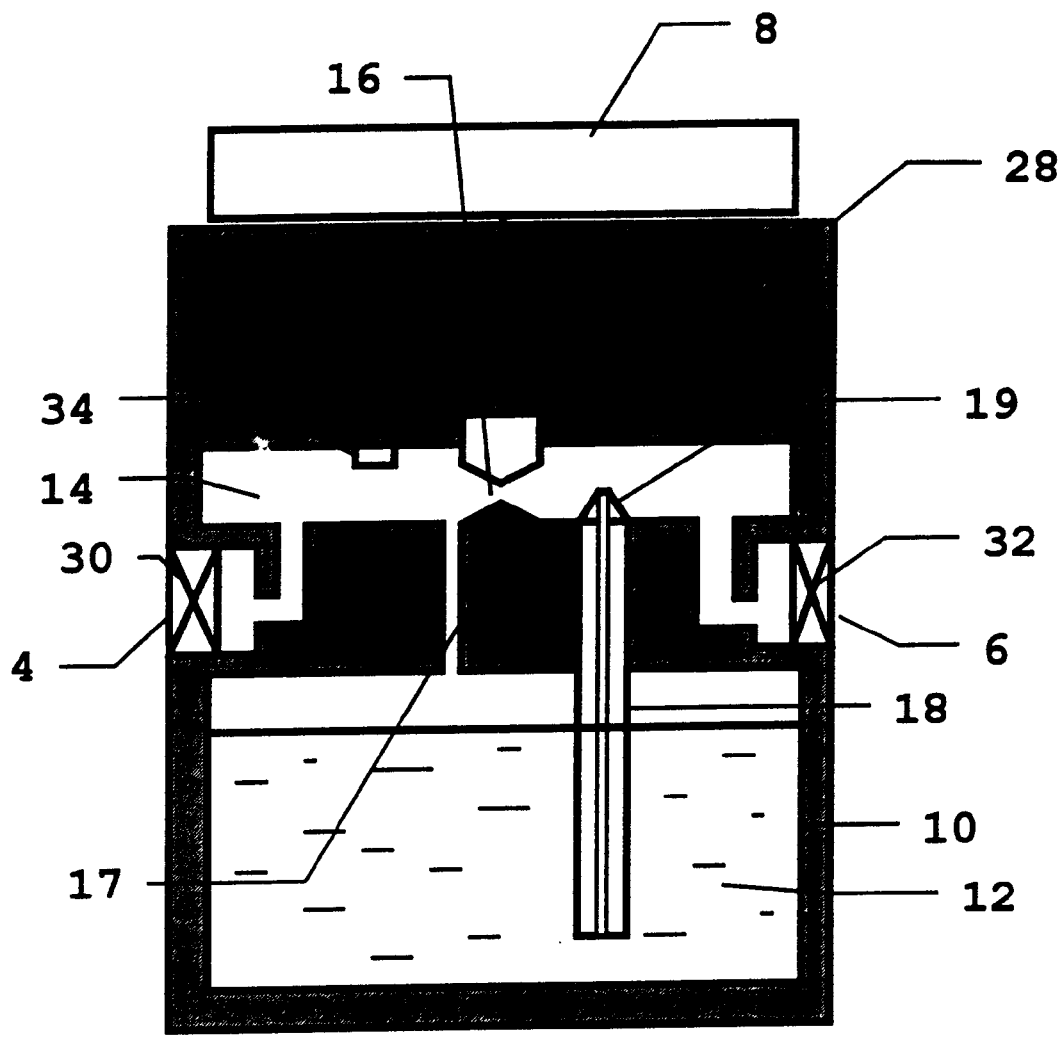
FIG. 2 shows a second embodiment of a vaporizer according to the invention.

FIG. 2 shows a second embodiment of a vaporizer 28 according to the invention. All parts and components identical to those in FIG. 1 have the same designations.

The vaporizer 28 has an inlet 4, a gas flow passage 14 and an outlet 6. The gas flow passage 14 is connected to a chamber 10 for anesthetic 12 by a first connection 17 upstream from the adjustable throttle 16 and by a second connection 18 downstream from the adjustable throttle 16.

The adjustable throttle 16 is electronically regulated by a control 8. The second connection is formed by a capillary tube with a nozzle 19.

This embodiment differs from the previous embodiment, apart from the electronic coupling of the control 8 and the adjustable throttle 16, in the following respects.

An inlet valve 30 is arranged in the immediate proximity of the inlet 4 and may be a mechanical or electronic valve. It can also be physically located in a coupling section (not shown) for gas to be sent to the vaporizer 28.

An outlet valve 32 is arranged in the immediate proximity of the outlet 6 and is electronically controlled. The control signal for the outlet valve 32 is obtained from a pressure meter 34 arranged upstream from the adjustable throttle 16. The outlet valve 32 can be physically located in a coupling section for receiving gas containing anesthetic.

If either of the outlet and inlet valves 30, 32, or both, are physically separated from the vaporizer 28, it should be equipped with a suitably devised check valve at the respective location. This is to ensure that no anesthetic, either in gaseous or liquid form, is able to leak out of the vaporizer 28 when it is detached from an anesthetic apparatus after use.

It should be noted that a version without an adjustable throttle 16 is also possible in both embodiments. The same dispensing effect can be achieved when the throttle 16 is fixed and a bypass flow past the vaporizer is regulated. When the throttle 16 is devised to deliver a maximal dose for a specific bypass flow, this bypass flow can then be regulated so the desired dose is dispensed.

Thus, a basic feature of the invention is that the outlet valve 22 or 32 is regulated by the pressure upstream from the throttle 16.

Combinations of the two embodiments are possible. For example, the vaporizer 2 in FIG. 1 can be devised with an electronic inlet valve 30, an electronic outlet valve 32 or electronic control of the adjustable throttle 16. In the corresponding manner, the vaporizer 28 in FIG. 2 can be devised with a fixed throttle 26 in the flow passage 14.

Although modifications and changes may be suggested by those skilled in the art, it is the intention of the inventors to embody within the patent warranted hereon all changes and modifications as reasonably and properly come within the scope of their contribution to the art.

We claim as our invention:

1. A vaporizer for vaporizing a liquid anesthetic, comprising:

a chamber containing liquid anesthetic;

an inlet for gas into which said liquid anesthetic is to be vaporized;

an outlet for said gas containing liquid anesthetic vaporized therein;

a gas flow passage between said inlet and said outlet;

a throttle in said gas flow passage;

a first connection between said chamber and said gas flow passage upstream of said throttle;

a second connection between said chamber and said gas flow passage downstream of said throttle; and an outlet valve disposed at said outlet and regulated by a pressure upstream of said throttle.

2. A vaporizer as claimed in claim 1 wherein said throttle comprises an adjustable throttle.

3. A vaporizer as claimed in claim 1 further comprising a gas control channel connecting said outlet valve to said gas flow passage upstream of said throttle for allowing pressure upstream of said throttle to act directly on said outlet valve to regulate said outlet valve.

4. A vaporizer as claimed in claim 3 wherein said throttle comprises a first throttle, and said vaporizer further comprising a second throttle disposed upstream of said first throttle between said gas control channel and said first connection.

5. A vaporizer as claimed in claim 1 further comprising a pressure meter connected to said outlet valve for measuring said pressure upstream of said throttle.

6. A vaporizer as claimed in claim 1 further comprising a bypass line connected between said inlet and said outlet for allowing an adjustable bypass flow of said gas at said inlet without passing through said gas flow passage.

7. A vaporizer as claimed in claim 1 wherein said second connection comprises a capillary tube having one end immersed in said liquid anesthetic in said chamber.

8. A vaporizer as claimed in claim 1 further comprising an inlet valve disposed at said inlet upstream of said throttle.

\* \* \* \* \*